United States Patent [19]
Borsari

[11] Patent Number: 4,859,319
[45] Date of Patent: Aug. 22, 1989

[54] DEVICE FOR MEASURING THE QUANTITY OF ULTRAFILTRATE ELIMINATED DURING A DIALYSIS TREATMENT

[75] Inventor: Gianni Borsari, Medolla Modena, Italy

[73] Assignee: Hospal AG, Basel, Switzerland

[21] Appl. No.: 894,846

[22] Filed: Aug. 8, 1986

[30] Foreign Application Priority Data

Aug. 9, 1985 [IT] Italy .............................. 53695/85[U]

[51] Int. Cl.⁴ ........................ B01D 13/00; B01D 37/04
[52] U.S. Cl. ...................................... 210/86; 210/116; 210/134; 210/321.65; 210/929
[58] Field of Search ............. 210/86, 104, 137, 195.2, 210/257.2, 321.2, 321.3, 929, 116, 134, 321.65

[56] References Cited

U.S. PATENT DOCUMENTS

| | | | |
|---|---|---|---|
| 2,611,269 | 9/1952 | Harstick et al. | 73/219 |
| 3,946,731 | 3/1976 | Lichtenstein | 128/214 R |
| 4,113,614 | 9/1978 | Rollo et al. | 210/321.3 X |
| 4,267,040 | 5/1981 | Schael | 210/321.2 X |
| 4,267,041 | 5/1981 | Schael | 210/109 |
| 4,275,726 | 6/1981 | Schael | 128/213 A |
| 4,372,846 | 2/1983 | Yamagami et al. | 210/86 |
| 4,397,747 | 8/1983 | Ikeda | 210/321.1 X |

FOREIGN PATENT DOCUMENTS

| | | |
|---|---|---|
| 765258 | 5/1934 | France . |
| 2087416 | 12/1971 | France . |
| 2472936 | 7/1981 | France . |

*Primary Examiner*—W. Gary Jones
*Assistant Examiner*—Linda S. Evans
*Attorney, Agent, or Firm*—Finnegan, Henderson, Farabow, Garrett & Dunner

[57] ABSTRACT

A device for measuring the quantity of ultrafiltrate eliminated during a dialysis treatment. The device comprises two vessels of a known capacity wherein the ultrafiltrate coming from a pump is alternately received and then discharged by means of valves. The device further comprises two level measuring sensors which each emit a signal each time the ultrafiltrate attains a predetermined level in the corresponding vessel. Such sensors are connected to a processing and count control mechanism for analyzing the above-mentioned signals and for establishing the quantity of ultrafiltrate eliminated by the pump.

11 Claims, 1 Drawing Sheet

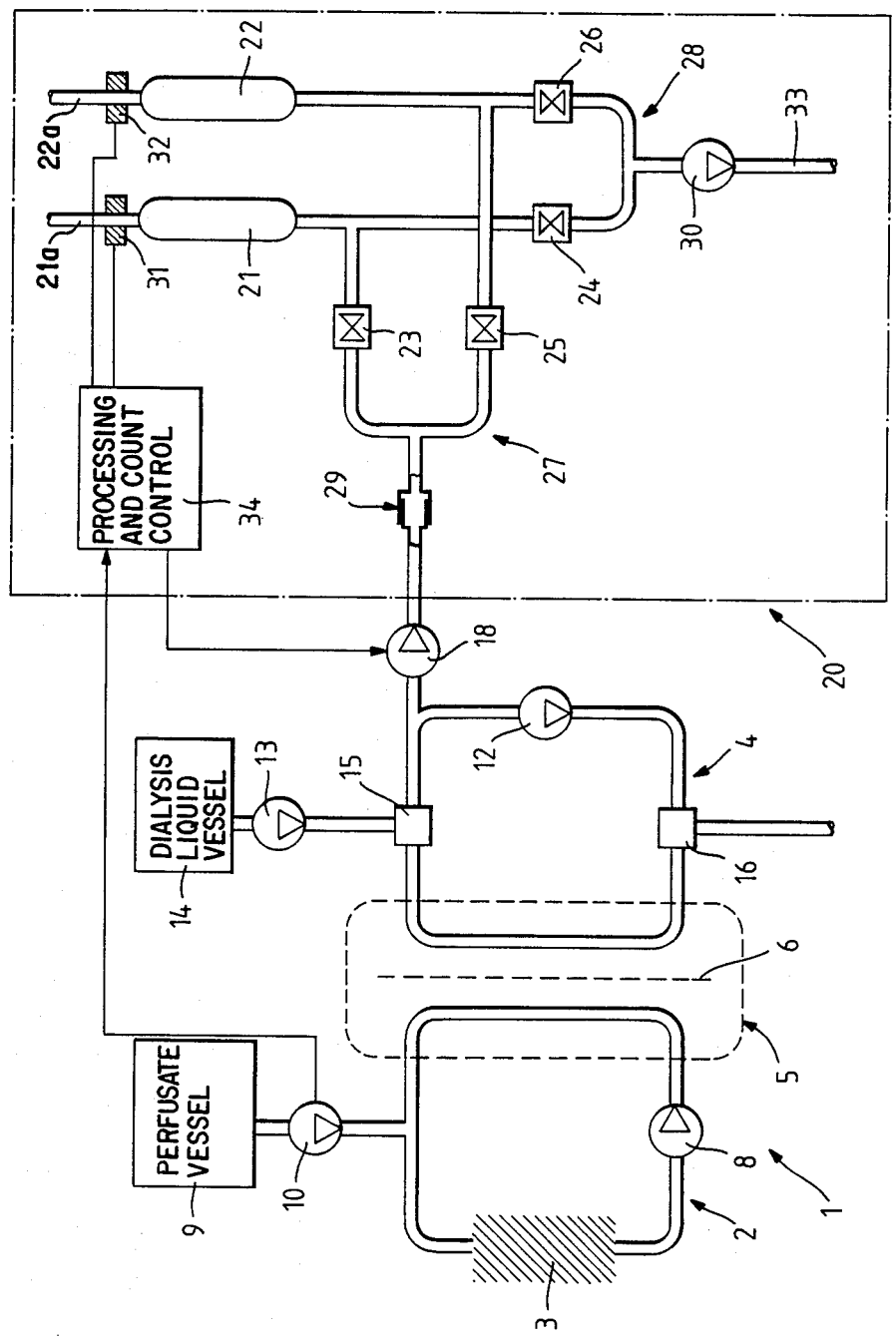

DEVICE FOR MEASURING THE QUANTITY OF ULTRAFILTRATE ELIMINATED DURING A DIALYSIS TREATMENT

BACKGROUND OF THE INVENTION

The present invention relates to a device or system for measuring the quantity of ultrafiltrate eliminated during a dialysis treatment.

The current practice for measuring the quantity of ultrafiltrate eliminated during a dialysis treatment involves placing a graduated vessel downstream from the ultrafiltration pump to collect the ultrafiltrate. The quantity of ultrafiltrate is controlled by manually reading the level reached by the ultrafiltrate in the vessel and, on the basis of this information, adjusting the speed of the pump to regulate the rate of ultrafiltration.

Clearly, a control system of this type has significant disadvantages. Errors can occur in reading the graduations of the vessel. Moreover, the system does not allow the ultrafiltration process to be controlled automatically.

SUMMARY OF THE INVENTION

The object of the present invention is to provide a device or system that overcomes the disadvantages of the conventional methods of measuring the quantity of ultrafiltrate eliminated during a dialysis treatment.

Additional objects and advantages of the invention will be set forth in part in the description that follows and in part will be obvious from the description or may be learned from the practice of the invention. The objects and advantages may be realized and obtained by means of the instrumentalities and combinations particularly pointed out in the appended claims.

To achieve the objects and in accordance with the purpose of the invention, disclosed herein is a device or system for measurement of the quantity of ultrafiltrate eliminated by means of a pump during a dialysis treatment comprising: first and second vessels for collecting the ultrafiltrate; ultrafiltrate discharge means connected to the vessels; first valve means operatively connected between the output of the pump and the vessels for filling the vessels; second valve means operatively connected between the vessels and the ultrafiltrate discharge means for emptying the vessels; sensing means operatively connected to each of the vessels for generating separate electrical signals in response to predetermined quantities of ultrafiltrate in each of the vessels; and processing and count control means connected to the first and second valve means and the sensing means and responsive to the electrical signals, for actuating the first and second valve means for alternately obtaining a simultaneous connection of (1) the first vessel to the output of the pump and the second vessel to the ultrafiltrate discharge means, and (2) the second vessel to the output of the pump and the first vessel to the ultrafiltrate discharge means, whereby the quantity of ultrafiltrate eliminated by the pump can be determined by accumulating a count of the number of times that the vessels are filled.

BRIEF DESCRIPTION OF THE DRAWING

The accompanying drawing, which is incorporated in and constitutes a part of this specification, illustrates one embodiment of the invention and, together with the description, serves to explain the principles of the invention. The drawing is a functional block diagram of a dialysis apparatus, comprising a subsystem wherein blood from a patient circulates, a subsystem wherein dialysis liquid circulates, a dialyser therough which both subsystems pass, and the present invention for measuring the quantity of ultrafiltrate eliminated.

DETAILED DESCRIPTION OF THE PREFERRED EMBODIMENT

Reference will now be made in detail to the present preferred embodiment of the invention, an example of which is illustrated in the accompanying drawing.

In the drawing, the numeral 1 designates the dialysis apparatus as a whole, having essentially a first subsystem 2 wherein the blood from a patient, designated by reference 3, can circulate and a second subsystem 4 wherein the dialysis liquid is caused to circulate. Subsystems 2 and 4, which function in a conventially known manner, pass through a conventional dialyser 5 having a semi-permeable diaphragm or membrane 6.

The subsystem 2 includes a pump 8, for example, a peristaltic type, capable of causing the blood to circulate and receiving "perfused" liquid containing various substances during the dialysis treatment. The perfusate is contained in a suitable vessel 9 which communicates with the subsystem 2 by means of a perfusion pump 10.

The subsystem 4 also includes a pump 12 capable of causing the dialysis liquid to circulate, subsystem 4 being itself supplied by a pump 13, which draws off the dialysis liquid from a suitable container 14 and delivers it into the subsystem 4 by means of a conventional dispensing device 15. Subsystem 4 is also capable of discharging the dialysis liquid to the outside by means of a discharge device 16. Moreover, subsystem 4 communicates with the input side of a suction pump 18 whose object is to create low pressure in the subsystem 4 so as to obtain ultrafiltration of the blood. Subsystem 4 must be made of a type of material which is essentially not subject to elastic deformation.

In accordance with the present invention, the measurement of the ultrafiltrate eliminated by means of pump 18 is effected by means of a device designated by reference 20 as a whole. The device includes first and second vessels 21, 22 for holding the ultrafiltrate and ultrafiltrate discharge means connected to the vessels.

As embodied herein, the two vessels 21, 22 for holding the ultrafiltrate are formed by two cylindrical reservoirs. The ultrafiltrate discharge means comprises a pump 30 and a discharge tube 33. The vessels communicate respectively with the output side of the pump 18 and with the discharge tube 33 by way of first valve means operatively connected between the output of pump 18 and vessels 21, 22, and second valve means operatively connected between the vessels 21, 22 and discharge pump 30.

As embodied herein, the first valve means comprises valves 23 and 25 and the second valve means comprises valves 24 and 26. More particularly, downline from the vessels 21, 22 there are disposed the ends of two fork-shaped tubes 27, 28 whose common portions communicate respectively with the output side of pump 18 by means of a connecting joint 29 and with the discharge tube 33 by means of a pump 30. Preferably, the valves are operated by electrical signals.

Operatively connected to the vessels 21, 22, respectively, are sensing means capable of indicating the presence of a predetermined quantity of ultrafiltrate, e.g., by emitting an electrical signal when the ultrafiltrate in the vessel reaches a predetermined level. Each of the vessels 21, 22 is provided with an extension 21a, 22a extending above its respective vessel and having a cross-section smaller than the cross-section of the vessel below the extension, and the sensing means consisting essentially of a sensor 31, 32 is operatively connected to its respective extension. As embodied herein, the sensing means can be ultrasonic, optical, or capacitive sensors 31, 32. Ultrasonic sensors are preferred.

In addition to the vessels, the ultrafiltrate discharge means, the valve means, and the sensing means, the measurement device of the present invention further includes processing and count control means 34 connected to valves 23, 24, 25, 26. The terminal of each sensor 31, 32 is also connected to the input of processing and count control means 34 which, includes a conventional counter capable of counting the number of electrical signals received from the sensors 31, 32 to make it possible to determine, as illustrated below, the quantity of ultrafiltrate eliminated by means of the pump 18.

The processing and count control means 34 also receives signals from the pump 10 relating to the quantity of liquid perfused and emits signals controlling the pump 18 and, therefore, the amount of ultrafiltrate. Processing and count control means 34 also emits electrical signals that control the relative positions of the electrically operated valves 23, 24, 25, 26. In particular, the valve 23 is actuated from its open position to its closed position in parallel with the valve 26. Similarly, the valves 24 and 25 are actuated in parallel. Thus, while one of the two vessels 21, 22 is being filled, the other is being emptied and vice versa. That is, processing and count control means 34 is adapted, in a conventionally known manner, to actuate valves 23, 24, 25, 26 for alternatively obtaining a simultaneous connection of (1) vessel 21 to pump 18 and vessel 22 to discharge pump 30, and (2) vessel 22 to pump 18 and vessel 21 to discharge pump 30.

When the device of the present invention is used, the weight loss which the patient should sustain during the dialysis treatment is stored in the memory of the processing and count control means 34. Then treatment is commerced during which the pump 10 continuously supplies the processing and count control means 34 with the data concerning the quantities perfused. The processing and count control means 34 then regulates the ultrafiltration by acting on the pump 18 on the basis of the data received via the sensors 31, 32.

More particularly, the dialysis liquid is caused to circulate in subsystem 4 by means of the pump 12, which liquid is periodically replaced by operation of conventional switching devices 15 and 16 and by activation of the pump 13. Moreover, the pump 18 creates low pressure in the subsystem 4, which provides the conditions for obtaining the ultrafiltration in a conventionally known manner. The ultrafiltrate, which is eliminated by the pump 18, is sent, for instance, first into the vessel 21, the electrically operated valves 24 and 25 being kept closed and the electrically operated valves 23 and 26 being kept open. In this way, the ultrafiltrate level within the vessel 21 rises gradually until it reaches a predetermined level detected by the sensor 31, at which level the precise quantity of ultrafiltrate in vessel 21 is known. Correspondingly, the opening of the valve 26 allows the ultrafiltrate contained in the vessel 22 to flow out through the discharge tube 33 by operation of the pump 30.

When the ultrafiltrate level within vessel 21 attains the level detected by the sensor 31, the latter transmits an electrical signal to the processing and count control means 34, which analyzes the electrical signal and reverses the control signals to the electrically operated valves 23, 24, 25, 26 so as to discharge the predetermined quantity of ultrafiltrate contained in the vessel 21 and to allow the vessel 22 to be filled up to a predetermined level detected by the sensor 32, at which level the precise quantity of ultrafiltrate in vessel 22 is known. In turn, the signal emitted by sensor 32 is registered by the processing and count control means 34, which initiates a new cycle in the actuations of the above mentioned valves.

The quantity of ultrafiltrate eliminated by pump 18 is, thus, determined by accumulating a count of the number of times vessels 21, 22 are filled to the known quantities detected by sensors 31, 32.

In the case where a fault would prevent the device 20 from functioning normally, it is possible to disconnect it from pump 18 at the connecting joint 29. The discharge tube of the pump 18 can then be connected to a graduated vessel of a conventional type.

A device having the characteristics of the device 20 and made according to the present invention will have several readily recognized advantages over the conventional devices of this type currently in use. Above all, the measurement of the quantity of ultrafiltrate affords a high degree of accuracy, depending essentially on the volume of vessels 21, 22, and it is not affected by a subjective reading of the level in the vessels. Moreover, it is possible to obtain an accurate measure of the decrease in the patient's weight at any time during the dialysis treatment, since the volume of liquid perfused into the patient in the subsystem 2 and the volume of ultrafiltrate eliminated from the subsystem 4 are known at any given time.

It will be apparent to those skilled in the art that various modifications and variations can be made to the processes and products of the present invention. Thus, it is intended that the present invention cover the modifications and variations of this invention, provided they come within the scope of the appended claims and their equivalents.

What is claimed is:

1. A device for measuring the quantity of ultrafiltrate eliminated by means of an ultrafiltrate pump during a dialysis treatment, comprising:

an ultrafiltrate supply conduit for connecting to the output of said ultrafiltrate pump;

first and second vertically-arranged vessels for collecting said ultrafiltrate, each having an upper portion and a lower portion;

means defining an opening in said lower portion of each of said vessels in flow communication with said supply conduit;

ultrafiltrate discharge means in flow communication with each of said openings;

first valve means in said ultrafiltrate supply conduit between the output of said ultrafiltrate pump and each of said openings;

second valve means connected to said ultrafiltrate discharge means;

sensing means consisting essentially of two sensors each operatively connected to one of said vessels for detecting the presence of a predetermined quantity of ultrafiltrate collected in each of said vessels by detecting when the ultrafiltrate reaches a predetermined level in each vessel and for generating separate electrical signals when said predetermined quantity is attained in each of said vessels; and processing and count control means operatively connected to each of said first and second valve means and to said sensing means and responsive to said separate electrical signals for actuating said first and second valve means to alternately obtain a simultaneous connection of (1) said opening in said first vessel to the output of said ultrafiltrate pump and said opening in said second vessel to the said ultrafiltrate discharge means, and (2) said opening in said second vessel to the output of said ultrafiltrate pump and said opening in said first vessel to said ultrafiltrate discharge means, whereby the quantity of ultrafiltrate eliminated by said ultrafiltrate pump can be determined by accumulating a count of the number of times said vessels are filled.

2. A device according to claim 1, further comprising a disconnect means connected to said ultrafiltrate supply conduit between said first valve means and said ultrafiltrate pump allowing said ultrafiltrate pump and said first valve means to be disconnected from each other.

3. A device according to claim 1 wherein said ultrafiltrate discharge means comprises an auxiliary pump and a discharge tube, said auxiliary pump interposed between said second valve means and said discharge tube.

4. A device according to claim 1, wherein said sensors are ultrasonic sensors.

5. A device according to claim 1, wherein said sensors are optical sensors.

6. A device according to claim 1, wherein said sensors are capacitive sensors.

7. A device according to claim 1, wherein said sensors consist of a first sensor positioned in said upper portion of said first vessel and a second sensor positioned in said upper portion of said second vessel.

8. A device according to claim 1, wherein each of said valve means comprises electrically operated valves controlled by said processing and count control means.

9. A device according to claim 1, wherein said first valve means comprises a first valve operatively connected between said output of said ultrafiltrate pump and said first vessel and a second valve operatively connected between said output of said ultrafiltrate pump and said second vessel, and wherein said second valve means comprises a third valve operatively connected between said first vessel and said ultrafiltrate discharge means and a fourth valve operatively connected between said second vessel and said ultrafiltrate discharge means, said processing and count control means for actuating said first and second valve means to alternately obtain a simulataneous opening of (1) said first valve to said pump and said fourth valve to said ultrafiltrate discharge means and (2) said second valve to said pump and said third valve to said ultrafiltrate discharge means.

10. A device according to claim 1, wherein said processing and count control means is for operatively connection to said ultrafiltrate pump and includes means for transmitting an actuating signal to said pump.

11. The device according to claim 1, wherein each of said vessels is further provided with an extensin above the vessel having a cross-section smaller than the cross-section of the vessel below the extension, wherein each said sensor of said sensing means is operatively connected to a corresponding one of said extensions.

* * * * *

UNITED STATES PATENT AND TRADEMARK OFFICE
CERTIFICATE OF CORRECTION

PATENT NO. : 4,859,319

DATED : August 22, 1989

INVENTOR(S) : BORSARI

It is certified that error appears in the above-identified patent and that said Letters Patent is hereby corrected as shown below:

Claim 10, line 3, change "nection" to --necting--; and

Claim 11, line 2, change "extensin" to --extension--.

Signed and Sealed this

Thirty-first Day of July, 1990

Attest:

HARRY F. MANBECK, JR.

*Attesting Officer*      *Commissioner of Patents and Trademarks*